United States Patent
Smits

(10) Patent No.: US 7,831,312 B2
(45) Date of Patent: Nov. 9, 2010

(54) FLOATING ADAPTER FOR USE WITH AUXILIARY LEAD ASSEMBLY

(75) Inventor: Karel F. A. A. Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 1057 days.

(21) Appl. No.: 11/537,257

(22) Filed: Sep. 29, 2006

(65) Prior Publication Data

US 2008/0082138 A1    Apr. 3, 2008

(51) Int. Cl.
*A61N 1/05* (2006.01)
*A61N 1/39* (2006.01)

(52) U.S. Cl. .......................... 607/116; 607/119; 607/5

(58) Field of Classification Search ............. 607/36–37, 607/115–119, 129–130
See application file for complete search history.

(56) References Cited

U.S. PATENT DOCUMENTS

| | | | | |
|---|---|---|---|---|
| 4,548,203 A | * | 10/1985 | Tacker et al. .................. | 607/27 |
| 4,932,407 A | * | 6/1990 | Williams ........................ | 607/5 |
| 5,012,806 A | * | 5/1991 | De Bellis ...................... | 607/33 |
| 5,095,903 A | * | 3/1992 | DeBellis ....................... | 607/33 |
| 5,385,574 A | * | 1/1995 | Hauser et al. .................. | 607/4 |
| 2006/0030224 A1 | | 2/2006 | DeGroot et al. | |

OTHER PUBLICATIONS

International Search Report, PCT/US2007/079638, May 27, 2008, 6 Pages.

\* cited by examiner

*Primary Examiner*—Carl H Layno
*Assistant Examiner*—Luther G Behringer
(74) *Attorney, Agent, or Firm*—Stephen W. Bauer

(57) ABSTRACT

A floating adapter is configured to electrically couple an auxiliary lead assembly to an implantable medical device including a canister. The floating adapter comprises a connector configured to receive an end of the auxiliary lead assembly, and a conductor having a proximal end and a distal end. The distal end of the conductor is coupled to the connector, and the proximal end of the conductor is coupled to a collector. The collector, the connector, and the conductor form a current flow path between the canister and the auxiliary lead assembly when the conductive body is implanted proximate the canister.

15 Claims, 6 Drawing Sheets

FLOATING ADAPTER FOR USE WITH AUXILIARY LEAD ASSEMBLY

TECHNICAL FIELD

This invention relates generally to an implantable medical device and, more particularly, to a floating adapter for electrically coupling an auxiliary lead assembly to an implantable medical device, such as an implantable cardioverter defibrillator.

BACKGROUND OF THE INVENTION

Implantable cardioverter defibrillators (ICDs) have been developed that may deliver low level electrical therapy to help pace a patient's heart and, if necessary, deliver high level electrical therapy to treat ventricular fibrillation. In general, an ICD comprises a pulse generator that receives the proximal end of an elongated and flexible lead assembly. The distal end of the lead assembly carries one or more pacing electrodes and one or more coiled defibrillation electrodes. When the ICD is implanted within a patient, the lead assembly is disposed proximate the patient's heart. If a transvenous lead assembly is employed, the distal end of the lead assembly is positioned within one or more chambers of the heart (endocardial lead), on the surface of the heart (epicardial lead), or within the surrounding vasculature. If a subcutaneous lead assembly is employed, the distal end of the lead assembly is positioned adjacent the heart. The ICD is capable of identifying and distinguishing between the different types of arrhythmias to determine the proper treatment to apply. To accomplish this, the ICD utilizes the pacing electrodes, other sense electrodes, and/or the ICD's conductive canister to monitor bioelectric signals indicative of cardiac activity.

In a small percentage of cases, an undesirably high defibrillation threshold (i.e., the amount of electrical therapy required to restore a fibrillating heart to its normal rhythm) may require an implanted ICD to administer multiple defibrillating pulses before fibrillation is corrected. The defibrillation threshold is influenced by a number of factors, which may include patient anatomy, patient medication, and migration of the ICD canister and/or leads after implantation. An undesirably high defibrillation threshold is typically addressed by equipping an ICD with an auxiliary lead assembly, such as a subcutaneous defibrillation lead assembly. This may be done during the original implantation of the ICD or during a secondary operation. In either case, the auxiliary electrode assembly is physically attached to the ICD; i.e., the proximal end of the auxiliary electrode assembly is typically plugged into an unused connector port provided on the ICD. If no unused connector port exits, the surgeon may be required to make available a connector port by removing a non-vital lead assembly connected to the ICD or, if this is not possible, the surgeon may replace the entire ICD. If a second operation is required to attach an auxiliary lead assembly to a previously implanted ICD, the ICD is excavated before the auxiliary lead assembly may be physically attached thereto. ICD excavation increases the costs and risks associated with the operation.

Considering the foregoing, it should be appreciated that it would be desirable to provide a floating defibrillation lead assembly that does not require a physical connection to an implanted medical device and, therefore, may be conceivably used with an ICD (or other medical device) without connector ports and/or with a previously implanted ICD without requiring the excavation thereof. In addition, it should be appreciated that it would be desirable to provide a floating adapter that may adapt a standard auxiliary lead assembly (e.g., a subcutaneous defibrillation lead assembly) for electrical communication with the canister of an ICD without physical attachment thereto. Furthermore, other desirable features and characteristics of the present invention will become apparent from the subsequent detailed description of the invention and the appended claims, taken in conjunction with the accompanying drawings and this background of the invention. As used herein, the term ICD is intended in its broadest sense and includes any implantable medical device capable of delivering defibrillation therapy to a patient's heart.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed descriptions. The present invention will hereinafter be described in conjunction with the appended drawings, wherein like reference numerals denote like elements, and.

DETAILED DESCRIPTION OF THE EXEMPLARY EMBODIMENT

The following description is exemplary in nature and is not intended to limit the scope, applicability, or configuration of the invention in any way. Rather, the following description provides a convenient illustration for implementing various exemplary embodiments of the present invention. Various changes to the described embodiments may be made in either the function or the arrangement of the elements described herein without departing from the scope of the invention.

Figure 1:
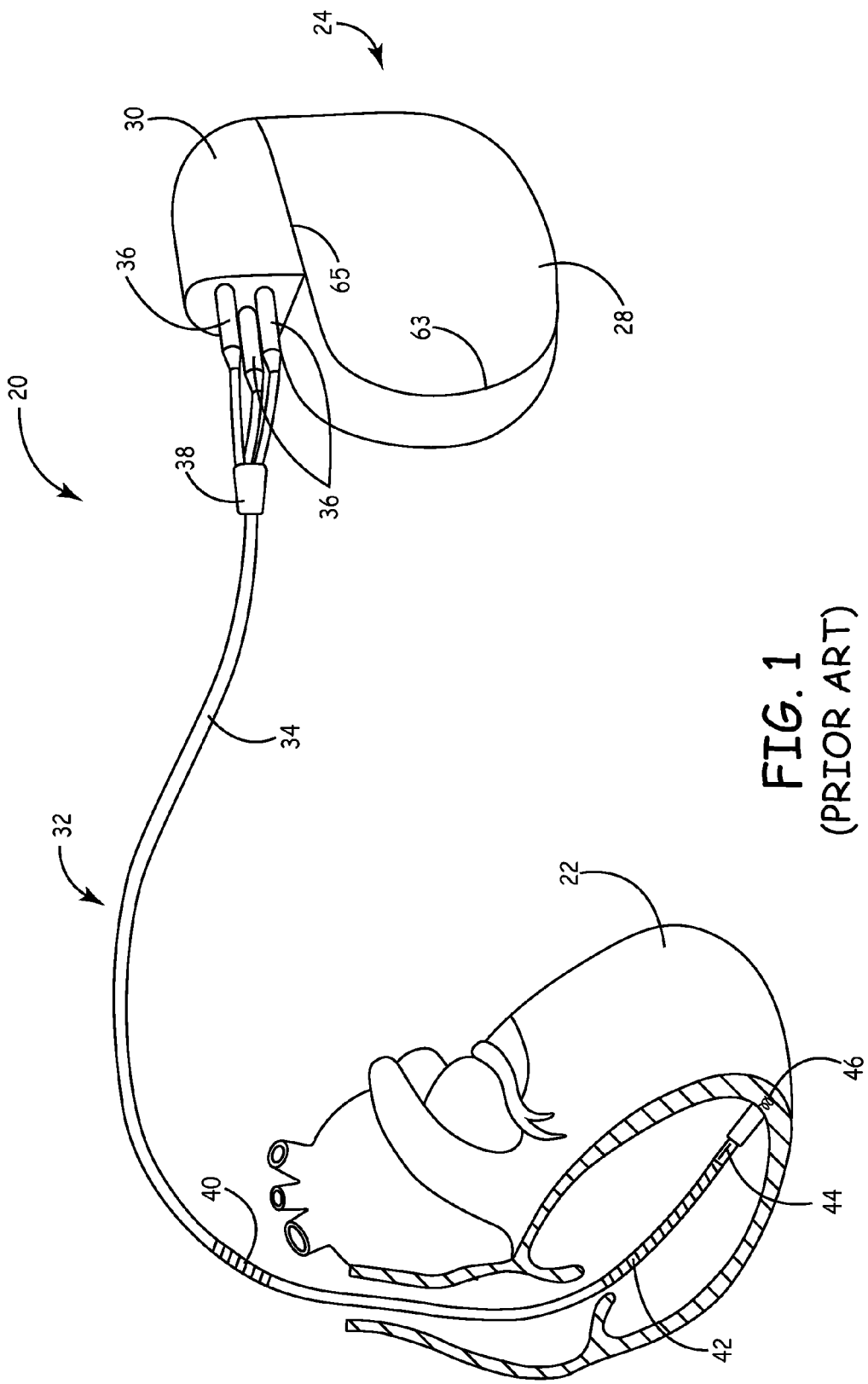
FIG. 1 is an isometric view of an implanted ICD in accordance with the prior art.

FIG. 1 is an isometric view of an implantable defibrillation device 20 after implantation proximate a patient's heart 22. Device 20 may be any implantable medical device capable of delivering electrical therapy to treat arrhythmic conditions experienced by heart 22; however, device 20 is preferably an implantable cardioverter defibrillator (ICD), which is capable of providing both defibrillation and pacing therapy to heart 22. For ease of description, device 20 will consequently be referred to as ICD 20 herein below. This notwithstanding, it should be remembered that the inventive floating adapter and floating auxiliary lead may be utilized with a wide variety of implantable medical devices, including implantable defibrillation devices and pacemakers other than ICDs.

ICD 20 comprises a pulse generator 24 including a conductive housing or canister 28 (e.g., titanium, stainless steel, aluminum, etc.) having control circuitry, a battery, and/or a capacitor housed therein. A connector block 30 is fixedly coupled to canister 28 and receives the proximal end of a lead assembly 32 therein. Lead assembly 32 may be endocardial, epicardial, subcutaneous, or a combination of these. In the illustrated embodiment, lead assembly 32 is an endocardial lead assembly, which has been inserted into heart 22 through the superior vena cava. Lead assembly 32 comprises an elongated insulated lead body 34, which comprises an insulative tubing (e.g., a polyurethane or silicon tube having an insulative silicon core) carrying a series of conductive filars. A plurality of electrodes is disposed on a distal portion of lead body 34. Each electrode is electrically coupled to a different one of the conductive filars traveling within lead body 34. The proximal end of lead assembly 32 comprises a plurality of lead legs 36. Lead legs 36 are joined to lead body 34 via a trifurcation 38, which directs each of the filars running within lead body 34 into a different one of lead legs 36. Lead legs 36 are each provided with a proximal connector end, preferably in the form of a standardized male IS-1(low voltage) or DF1 (high voltage) connector, which may be plugged into one of three connector ports provided in connector block 30. A setscrew block (not shown) may provided within connector block 30 and tightened (e.g., via a torque wrench) to secure the proximal ends of lead legs 36 within connector block 30. When leads legs 36 are received by connector block 30 in this manner, the control circuitry disposed within pulse generator 24 is electrically coupled to the distal sensing and therapy electrodes carried by endocardial lead assembly 32.

It will be appreciated by one skilled in the art that the number and type of electrodes carried by lead assembly 32 will vary in accordance with individual sensing, pacing, and/ or defibrillation needs. In the illustrated embodiment, lead assembly 32 caries four electrodes: a first elongated coil electrode 40, a second elongated coil electrode 42, a ring electrode 44, and an extendible helix electrode 46. Coil electrode 40 is positioned proximate the superior vena cava, and coil electrode 42 resides within the right ventricle of heart 22. In general, coil electrodes 40 and 42 may be straight and 50 to 150 millimeters in length, or coil electrodes 40 and 42 may be sigmoidal, coiled, or U-shaped and approximately 100 to 200 millimeters in length. Coil electrodes 40 and 42 are utilized primarily for providing defibrillation therapy to heart 22. In contrast, ring electrode 44 and extendible helix electrode 46 are utilized to provide low level pacing pulses to heart 22. In addition, ring electrode 44 and helix electrode 46 are utilized as sense electrodes, which cooperate with canister 32 to form a plurality of sensing vectors that measure bioelectric signals indicative of cardiac activity (e.g., atrial depolarization). When an arrhythmia is detected within heart 22, ICD 20 will determine the appropriate therapy to apply. For example, if ICD 20 determines that the registered bioelectric signals (in particular, the QRS complex) are indicative of ventricular fibrillation, ICD 20 will act as a defibrillator and cause coil electrode 40 and/or coil electrode 42 to deliver a high energy intrathoracic/transthoracic therapy across heart 22. If necessary, ICD 20 may also deliver high level emergency pacing between canister 28 and coil electrode 42. If, instead, ICD 20 determines the electrical signals to be indicative of a different type of arrhythmia (e.g., tachycardia, bradycardia, or atrial fibrillation), ICD 20 will act as a cardioverter and cause ring electrode 44 and/or helix electrode 46 to administer low level pacing therapy to heart 22.

As explained above, it is occasionally desirable or necessary to outfit an implanted medical device (e.g., ICD 20) with an auxiliary lead assembly. Physically connecting an auxiliary lead assembly to an implanted ICD is, however, an often cumbersome process that may not always be practicable. In accordance with a first embodiment of the present invention, FIG. 2 is an partial cutaway view of a floating adapter 50 that may be utilized to electrically couple an auxiliary lead assembly (e.g., a subcutaneous defibrillation lead assembly) to an ICD (or other implantable medical device) without physical connection.

Figure 2:
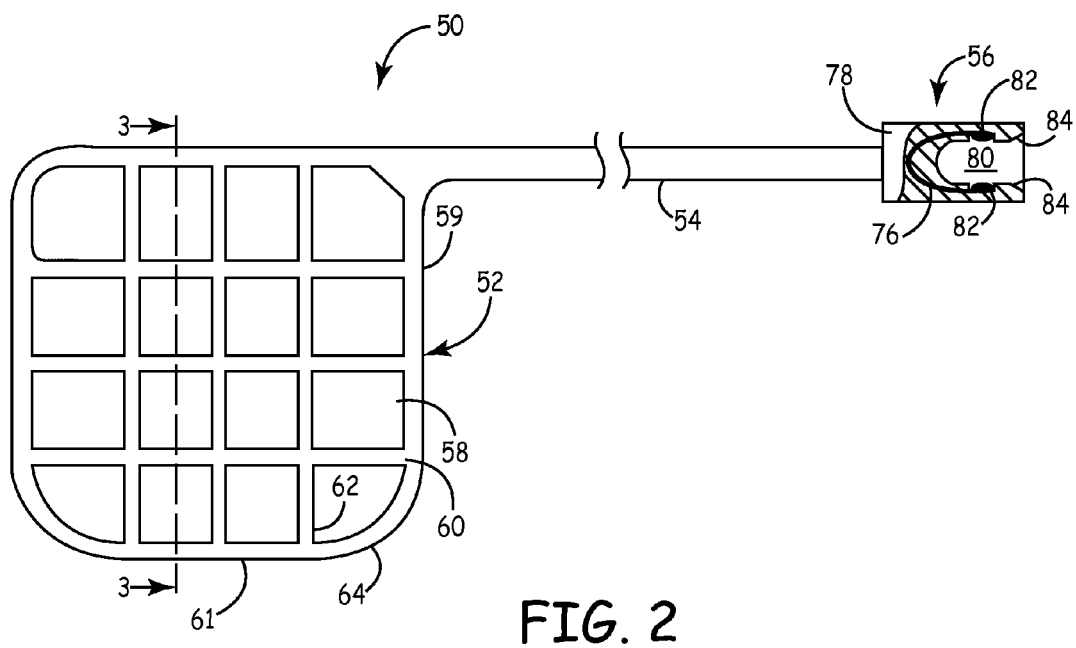
FIG. 2 is a partial cutaway view of a floating adapter in accordance with a first embodiment of the present invention.

As shown in FIG. 2, floating adapter 50 comprises three main components: a current collector 52, a conductor 54, and a connector 56. Collector 52 comprises a conductive body 58, which is preferably comprised of a metal or alloy plate (e.g., titanium alloy, stainless steel, etc.). Conductive body 58 may assume a wide variety of shapes and configurations as described in more detail below in conjunction with FIGS. 7-12. In the embodiment illustrated in FIG. 2, conductive body 58 comprises a generally flat and rectangular plate having rounded edges. The dimensions of conductive body 58 will vary in accordance with desired performance characteristics; however, it is preferable that certain dimensions of conductive body 58 (and, more generally, collector 52) are similar to those of the conductive canister of the implantable medical device with which floating adapter 50 is utilized. That is, the height and width of collector 52 (indicated as 59 and 61, respectively, in FIG. 2) are preferably substantially equal to the height and width of the canister's lateral projection (indicated as 63 and 65, respectively, in FIG. 1). The thickness of conductive body 58 will generally be substantially less than the thickness of the medical device's canister and is preferably on the order of a few tenths of a millimeter.

Although not essential to floating adapter 50, collector 52 may further include an insulative structure 60 (e.g., silicon rubber, polyurethane, etc.) disposed over a portion of conductive body 58. In certain embodiments, insulative structure 60 comprises a plurality of spacers that prevents conductive body 58 from directly contacting the canister of an implantable medical device, such as ICD 20 (FIG. 1), as such contact may interfere with the accurate monitoring of bioelectric signals. For example and as illustrated in FIG. 2, insulative structure 60 may comprise a network or lattice of raised ribs 62. Ribs 62 are disposed across the illustrated face of conductive body 58 such that a grid of windows is formed through insulative structure 60. Insulative structure 60 may also be disposed across the opposing, non-illustrated face of conductive body 58 in a similar fashion. In this manner, conductive body 58 may be exposed through either side of collector 52, which may improve the electrical performance characteristics of collector 52. Insulative ribs 62 are formed to have a thickness sufficient to prevent contact between a medical device's conductive canister and conductive body 58. This may be most readily appreciated by referring to FIG. 3, which is a cross-sectional view of collector 52 taken along line 3-3 (FIG. 2).

In the illustrated embodiment, insulative structure 60 also comprises a collar or frame 64 around the outer peripheral edge of conductive body 58. Frame 64 may have a thickness substantially equal to that of ribs 62 and may be integrally formed therewith. The inclusion of frame 64 provides multiple advantages to floating adapter 50; e.g., frame 64 protects surrounding tissue from the relatively sharp outer edge of conductive body 58. In addition, frame 64 shields the surrounding tissue from high current densities that may occur at the outer edge of conductive body 58. Furthermore, frame 64 may serve as anchoring feature that deters the migration of floating adapter 50 after implantation. Finally, frame 64 may serve as an insulative spacer, which, together with ribs 62, prevents conductive body 58 from contacting the canister of an implantable medical device as explained above.

Figure 3:
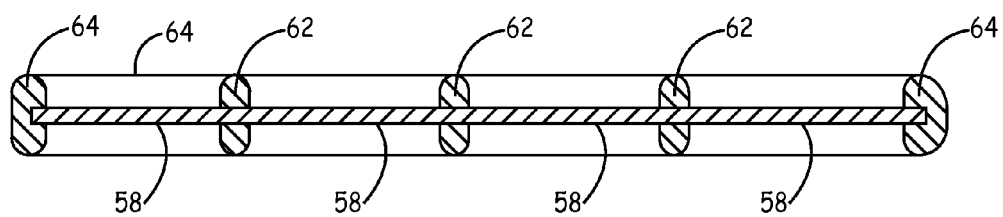
FIG. 3 is a cross-sectional view of the floating adapter shown in FIG. 2 taken along line 3-3.
Figure 4:
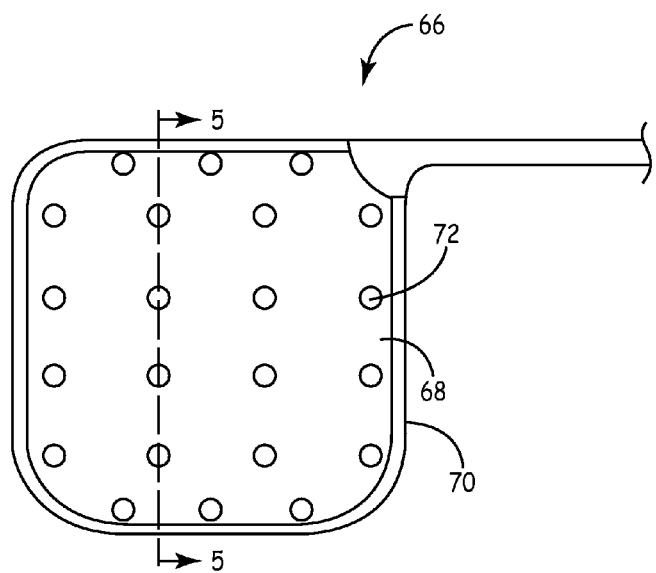
FIG. 4 is a plan view of a floating adapter in accordance with a second embodiment of the present invention.
Figure 5:
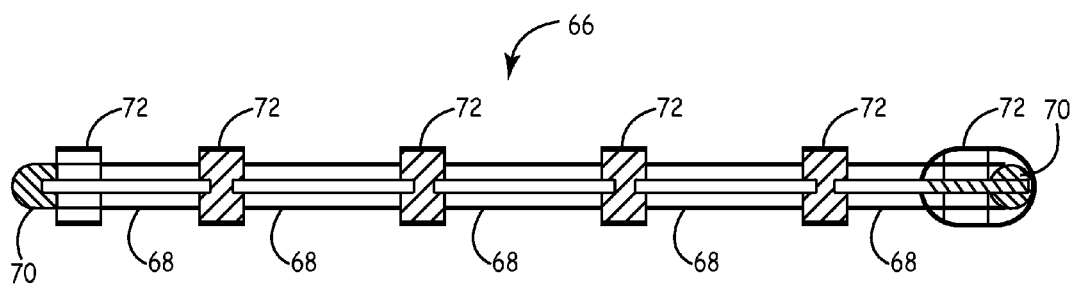
FIG. 5 is a cross-sectional view of the floating adapter shown in FIG. 4 taken along line 5-5.

Although adapter 50 utilizes a frame 64 comprising an insulative material, other embodiments of the floating adapter may employ a frame formed from a non-insulative material. This point is illustrated in FIGS. 4 and 5, which are plan and cross-sectional views of a collector 66 in accordance with a second embodiment of the present invention. Collector 66 including a conductive body 68, which may comprise of a flattened metal or alloy plate similar in shape to conductive body 58 (FIGS. 2 and 3). A peripheral frame 70 is disposed around the outer edge of conductive body 68. Frame 70 is comprised of a conductive material (e.g., titanium alloy, stainless steel, etc.) and may be integrally formed with conductive body 68. Although frame 70 does not function as an insulative spacer as does frame 64 (FIGS. 2 and 3), frame 70 still serves to protect surrounding tissue and anchor floating adapter 50. Due to its conductive nature, frame 70 is prevented from contacting the canister of an implanted medical device by a plurality of insulator blocks 72, which are disposed over conductive body 68 at various spaced locations. As may be most easily appreciated in FIG. 5, insulator blocks 72 each have a thickness greater than that of conductive frame 70 so as to protrude beyond frame 70 and thus prevent contact with a medical device's canister.

Referring once again to FIGS. 2 and 3, floating adapter 50 further comprises an elongated insulated conductor 54 and a connector 56, which may be, for example, a standardized DF1 (high voltage) or IS-1 (low voltage) connector. A filar (not shown) extends through insulated conductor 54 and electrically couples conductive body 58 to a contact 76 contained within connector 56. In the illustrated embodiment, contact 76 comprises a spring clamp structure, which resides in a female connector body 78. Female connector body 78 includes a cavity 80 therein through which one or more portions of contact 76 are exposed as contact surfaces 82. A male connector of an auxiliary lead may be received within cavity 80 to electrically couple the auxiliary lead electrode or electrodes to conductive body 58 of collector 52. The proximal ends of connector body 78 may be chamfered as shown in FIG. 2 at 84 to facilitate reception of the male connector within cavity 80. As will be described more fully below, coupling an auxiliary lead to floating adapter 50 in this manner provides a low-resistance current flow path between the auxiliary lead electrode (or electrodes) and current collector 52 and, consequently, between the auxiliary lead electrode and the conductive canister of an implantable medical device residing proximate collector 52.

Figure 6:
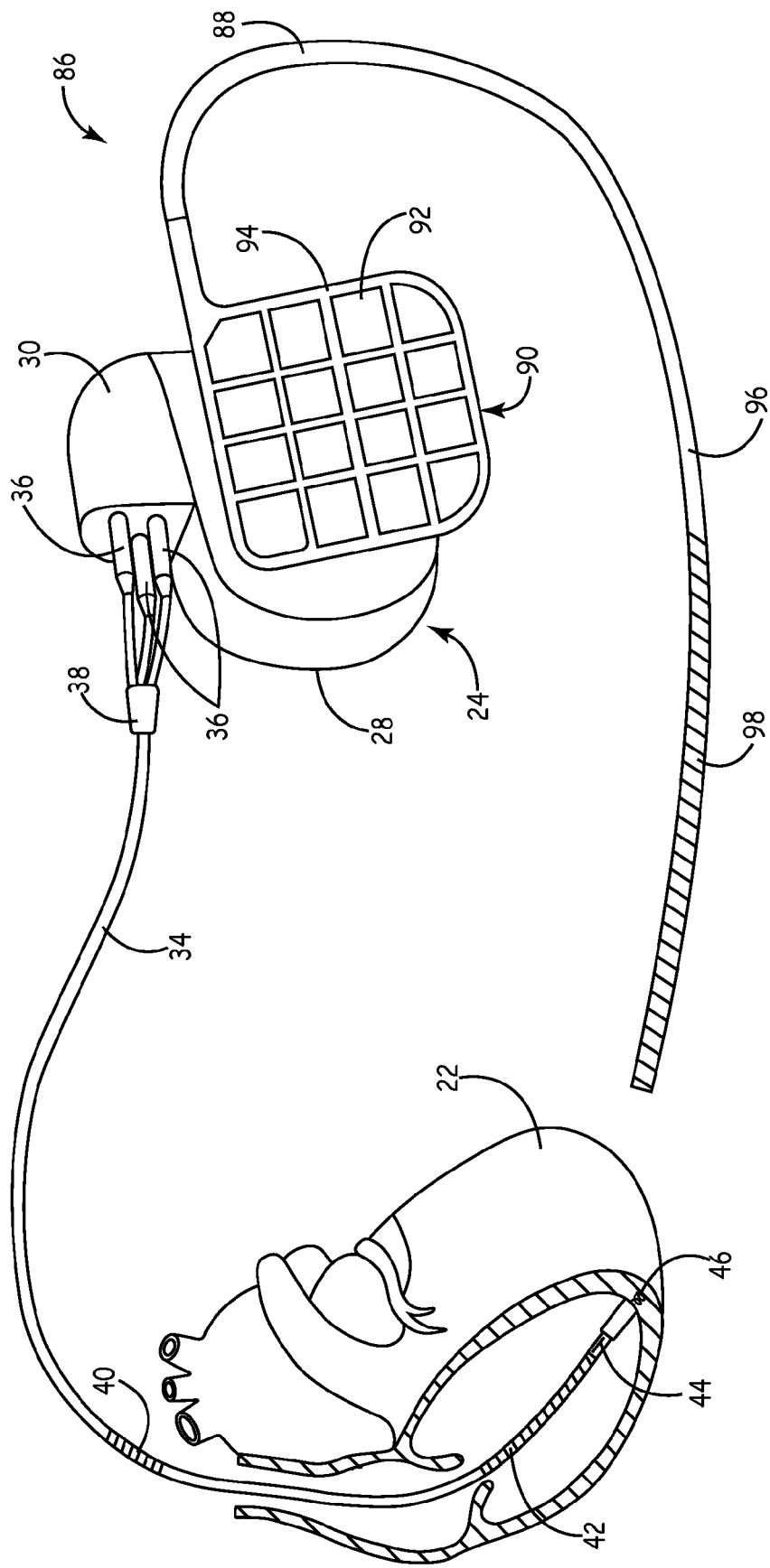
FIG. 6 is an isometric view of a floating auxiliary lead assembly implanted adjacent the ICD shown in FIG. 1 in accordance with a third embodiment of the present invention.

FIG. 6 is an isometric view of a floating auxiliary lead assembly 86 implanted proximate ICD 20 (FIG. 1) in accordance with a third embodiment of the present invention. Floating auxiliary lead assembly 86 assembly is similar to floating adapter 50 (FIGS. 2 and 3) in several respects; floating auxiliary lead assembly 86 assembly comprises a conductor 88 and a current collector 90 including a conductive body 92 (e.g., a metal plate) and an insulative structure 94 disposed over a portion of conductive body 92. However, unlike floating adapter 50, auxiliary lead assembly 86 does not include a connector; instead, auxiliary lead assembly 86 assembly further comprises a lead 96 including at least one electrode 98 (e.g., a coil electrode, a patch electrode, sigmoid-type electrode, etc.) disposed thereon. For example and as illustrated in FIG. 6, lead 96 may comprise a unipolar subcutaneous defibrillation lead having a defibrillation coil 98 disposed around a distal portion thereof. Lead 96 may also include one or more anchoring structures (not shown), such as an anchoring sleeve. Insulated conductor 88 preferably comprises an insulative (e.g., silicon) sheathing carrying one or more conductive filars, which electrically couple defibrillation coil 98 to conductive body 92.

Referring still to FIG. 6, it may be seen that floating auxiliary lead assembly 86 is implanted such that current collector 90 resides adjacent canister 28. For example, lead assembly 86 may be implanted in the surgically-produced ICD pocket such that a portion of collector 90 (e.g., insulative structure 94) contacts or nearly contacts canister 28. Alternatively, floating auxiliary lead assembly 86 may be implanted in a separate surgically-produced pocket adjacent and preferably in parallel with the ICD pocket such that collector 90 is separated from canister 28 by a thin wall of tissue. In either arrangement, collector 28 is ideally positioned such that conductive body 92 is approximately 2-10 millimeters away from canister 28 to minimize tissue resistance between conductive body 92 and canister 28. Lead 96 is positioned such that coil electrode 98 resides proximate a lower portion of heart 22; e.g., lead 96 may be placed in the left sub-auxiliary or dorsolateral thoracic wall proximate the left ventricle of heart 22.

Upon determining that heart 22 is experiencing ventricular fibrillation, ICD 20 will deliver defibrillation therapy to heart 22 as explained above. The defibrillation therapy may be applied between conductive canister 28 and coil electrode 42 residing within the right ventricle of heart 22. When therapy is applied in this manner, while the conductive body 92 and the defibrillation electrode 98 would not be electrically connected, the conductive body 92 of collector 90 will assume an electrical potential present in the tissue near the conductive body 92 and, at the same time, defibrillation electrode 98 will assume a potential present as an average in the tissue surrounding the defibrillation electrode 98. Assuming the potential of the canister 28 is zero percent and the potential of the right ventricular electrode 42 is 100 percent, the potential of the conductive body 92 would typically be in the range from zero to 10 percent and the potential of the defibrillation electrode 98 would typically be in the range of 30 to 50 percent of the total potential difference between canister 28 and right ventricular electrode 42. However, by electrically connecting the conductive body 92 and the defibrillation electrode 98 by a low resistance conductor 88, the potential of the conductive body 92 and the potential of the defibrillation electrode 98 are equalized close to the "unconnected" potential of the conductive body 92. This means the creation of potential differences between the conductive body 92 and defibrillation electrode 98 surfaces and their respective surrounding tissue. As a result of the difference in these potentials, current will flow from endocardial coil electrode 42 to subcutaneous coil electrode 98. From coil electrode 98, the current will flow through conductor 88, to conductive body 92 of collector 90 and, ultimately, from conductive body 92 to canister 28 of ICD 20. Floating auxiliary lead assembly 86 thus cooperates with ICD 20 to provide a low-resistance electrical path from endocardial coil electrode 42 to conductive canister 28. The provision of such a low-resistance current path improves current density distribution across the myocardium of heart 22 during therapeutic treatment (e.g., defibrillation) and, consequently, lowers the defibrillation threshold of ICD 20.

Figure 7:
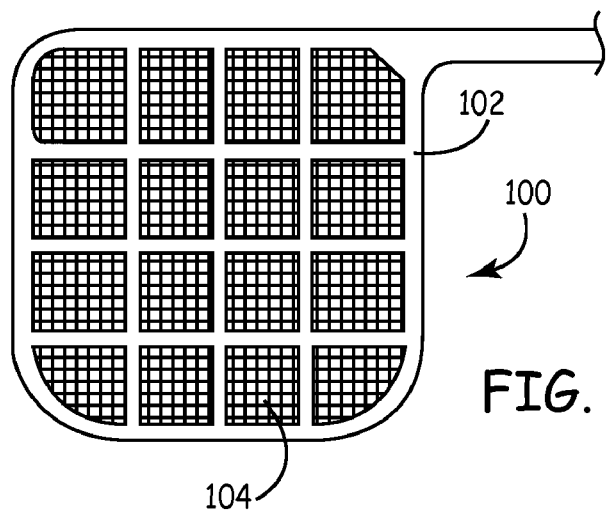
FIG. 7 is a plan view of a collector including a conductive body comprised of a wire mesh.

The foregoing has described floating adapters and a floating auxiliary lead assembly employing a collector comprised of a solid, plate-like body; however, it should be appreciated that the collector may assume a wide variety of shapes and configurations suitable for facilitating electrical communication with the canister of an implantable medical device. To further illustrate this point, FIGS. 7-12 illustrate a number of exemplary collectors assuming alternative forms. Referring first to FIG. 7, a collector 100 comprises an insulative structure 102 and a conductive body 104, which is similar to the conductive bodies employed by collector 52 (FIGS. 2 and 3), collector 66 (FIGS. 4 and 5), and collector 90 (FIG. 6). However, unlike the conductive bodies of these earlier-described collectors, conductive body 104 comprises an interwoven, flexible mesh of conductive wire.

Figure 8:
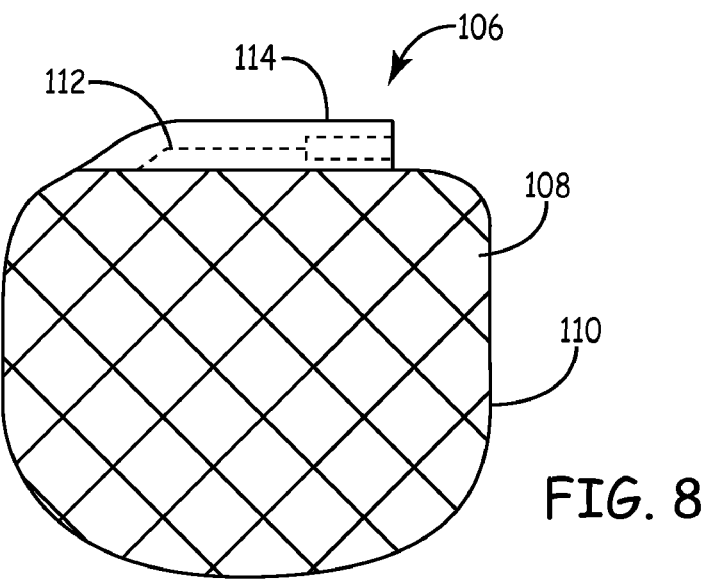
FIG. 8 is a plan view of a collector including a conductive body comprised of reticulate wire member encased by a conductive polymer.

FIG. 8 illustrates a collector 106 having a conductive body 108 comprised of a reticulate network of conductive wire similar to mesh conductive body 104 (FIG. 7). In contrast to conductive body 104, however, conductive body 108 is enveloped in a flexible encasement 110, which may comprise, for example, an electrically conductive polymeric material. As a further distinguishing feature, collector 106 includes a truncated conductor 112 and a connector 114 fixedly coupled to encasement 110.

Figure 9:
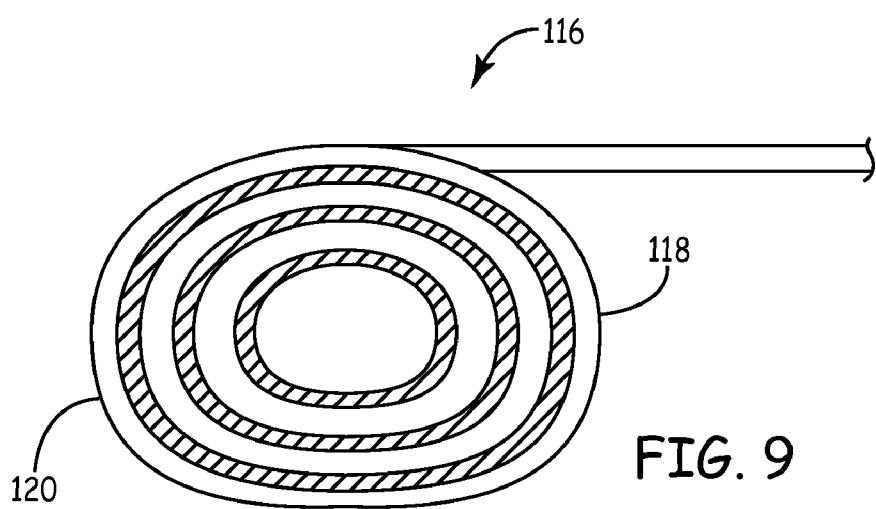
FIG. 9 is a plan view of a collector including a conductive body comprised of a plurality of concentric coils partially embedded in a non-conductive plate.

The collector of the inventive floating adapter/auxiliary lead assembly may also comprise one or more coiled wires. For example, FIG. 9 illustrates a collector 116 similar in structure to an epicardial patch electrode. Collector 116 comprises three concentric coils 118, which are supported by (e.g., partially embedded in) a non-conductive (e.g., silicon rubber) plate 120. Coils 118 are exposed through the illustrated face of plate 120 and may or may not be exposed through the non-illustrated opposing face of plate 120.

Figure 10:
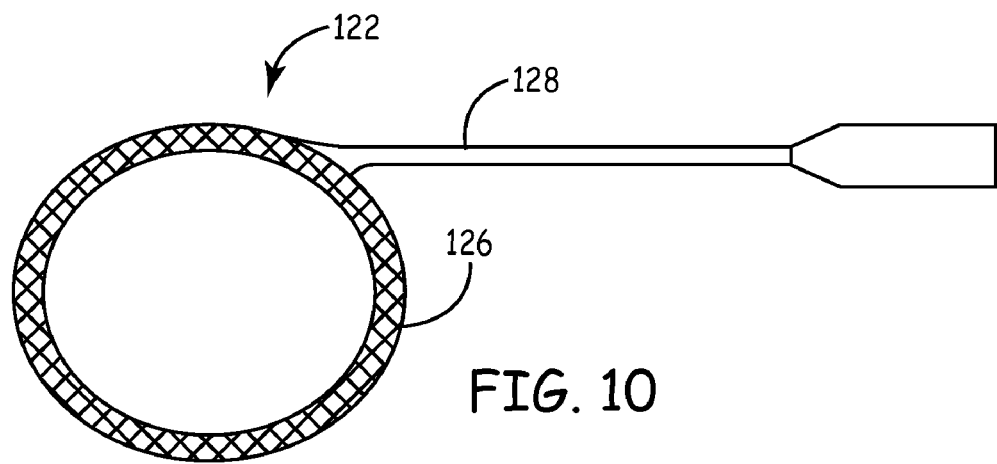
FIGS. 10, 11, and 12 are plan views of collectors including coiled conductive bodies in ring, clover, and curved configurations, respectively.
Figure 11:
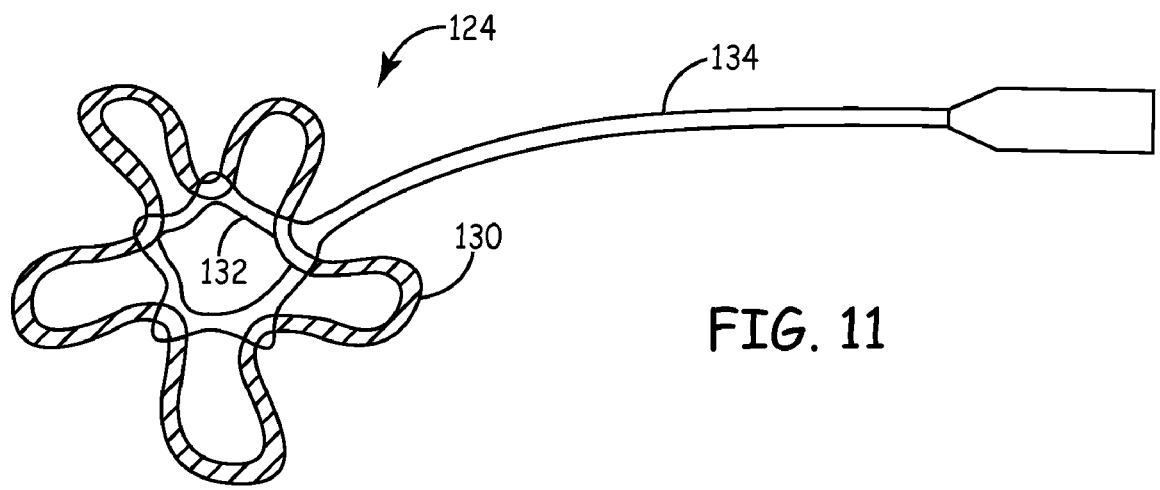

Certain embodiments of the inventive floating adapter/auxiliary lead assembly may include a collector employing one or more conductive coils that are not embedded in a supportive structure. FIG. 10, for example, illustrates a collector 122 comprising ring electrode 126 coupled to the distal end of a conductor 128. Similarly, FIG. 11 illustrates a coil electrode secured in a clover configuration by a central hub 132 (e.g., silicon), which is fixedly coupled to a conductor 134. Coil electrode 130 thus cooperates with central hub 132 to form a plurality of flexible lobes, preferably four to eight in total. If desired, coil electrode 130 may be wrapped around a silicone rubber core for added support.

Figure 12:
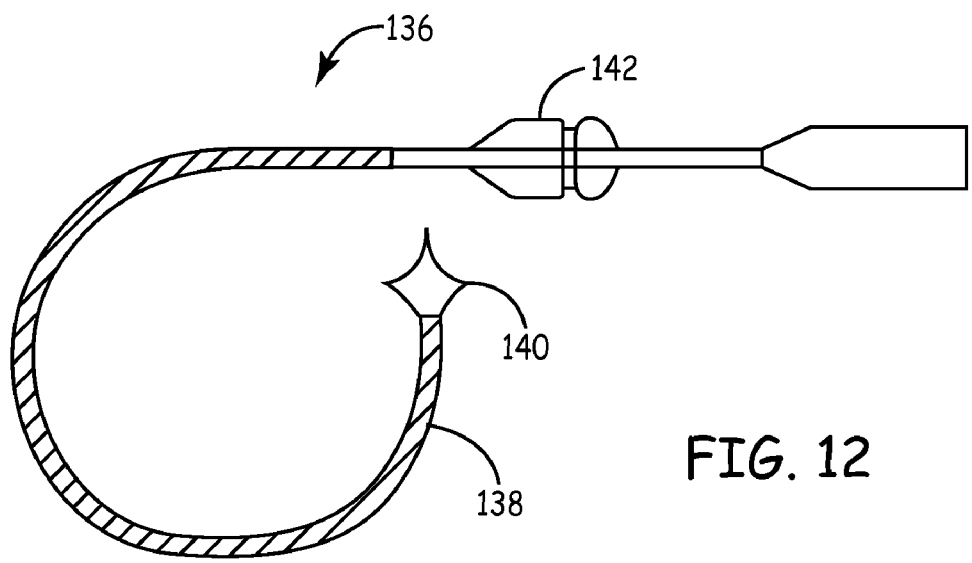

FIG. 12 illustrates a collector 136 having a conductive body comprising a flexible coil electrode 138, which, during implantation in the subcutaneous tissue, may be formed to a curve by pulling electrode 138 through a previously implanted temporary sheath or pulled with a standard pull wire along a subcutaneous pathway created with a curve needle (not shown). In a preferred embodiment, the length of coil electrode 138 is substantially equivalent to the circumference of the canister adjacent which coil electrode 128 is employed. Collector 136, or any of the other collectors or other components described above, may include one or more anchoring features. In the embodiment illustrated in FIG. 12, collector 136 includes two such anchoring features: a distal fixation 140, and an anchoring sleeve 142 disposed adjacent the proximal end of coil electrode 138.

In view of the above, it should be appreciated that a floating defibrillation lead has been provided that may be placed in electrical communication with the conductive canister of an ICD without being physically connected thereto. It should further be appreciated that a floating adapter has been provided capable of adapting a standard auxiliary lead assembly (e.g., a subcutaneous defibrillation lead assembly) for electrical communication with an ICD without physical attachment thereto. Although the invention has been described with reference to a specific embodiment in the foregoing specification, it should be appreciated that various modifications and changes can be made without departing from the scope of the invention as set forth in the appended claims. Accordingly, the specification and figures should be regarded as illustrative rather than restrictive, and all such modifications are intended to be included within the scope of the present invention.

The invention claimed is:

1. A floating adapter configured to electrically couple an auxiliary lead assembly to an implantable medical device including a conductive canister, comprising:
   a connector configured to receive an end of the auxiliary lead assembly;
   a conductor having a proximal end and a distal end, said distal end coupled to said connector; and
   a collector coupled to said proximal end, said collector, said connector, and said conductor forming a current flow path between the conductive canister and the auxiliary lead assembly when said conductive body is implanted proximate the conductive canister.

2. A floating adapter according to claim 1 wherein said collector comprises a plate-like body.

3. A floating adapter according to claim 1 wherein said collector comprises a mesh body.

4. A floating adapter according to claim 1 wherein said collector comprises:
   a network of conductive wires; and
   a conductive encasement substantially enveloping said network of conductive wires.

5. A floating adapter according to claim 1 wherein said collector comprises at least one coiled wire.

6. A floating adapter according to claim 5 wherein said collector further comprises an insulated central hub securing said at least one coiled wire in a clover formation.

7. A floating adapter according to claim 1 wherein the collector comprises:
   an electrically conductive body coupled to said conductor; and
   an electrically insulative structure disposed over a portion of said electrically conductive body.

8. A floating adapter according to claim 7 wherein said electrically insulative structure is disposed around at least a portion of the outer edge of said electrically conductive body, said insulative structure having a thickness substantially greater than that of said conductive body.

9. A floating adapter according to claim 7 wherein said electrically insulative structure comprises at least one insulative spacer.

10. A floating adapter according to claim 9 wherein said at least one spacer comprises a plurality of ribs disposed across said electrically conductive body.

11. A floating adapter configured to electrically couple an auxiliary lead assembly to an implantable medical device including a conductive canister, comprising:
    a connector configured to receive an end of the auxiliary lead assembly;
    a conductor having a proximal end and a distal end, said distal end coupled to said connector; and
    a collector coupled to said proximal end, said collector, said connector, and said conductor forming a current flow path between the conductive canister and the auxiliary lead assembly when said conductive body is implanted proximate the conductive canister; and
    wherein said collector has dimensions substantially equal to those of the lateral profile of the conductive canister.

12. A floating adapter configured to electrically couple an auxiliary lead assembly to an implantable medical device including a conductive canister, comprising:

a connector configured to receive an end of the auxiliary lead assembly;

a conductor having a proximal end and a distal end, said distal end coupled to said connector; and a collector coupled to said proximal end, said collector, said connector, and said conductor forming a current flow path between the conductive canister and the auxiliary lead assembly when said conductive body is implanted proximate the conductive canister;

wherein the collector comprises:

an electrically conductive body coupled to said conductor; and an electrically insulative structure disposed over a portion of said electrically conductive body; and wherein said collector includes first and second opposing faces, said electrically conductive body substantially exposed through each of said first and second opposing faces.

13. A floating adapter configured to electrically couple a subcutaneous lead assembly to an implantable cardioverter defibrillation (ICD) including a conductive canister and a defibrillation coil, the ICD configured to be implanted proximate a patient's heart, the floating adapter comprising:

a current collector configured to be implanted adjacent the canister, comprising:

a conductive body comprising first and second opposing faces each having dimensions substantially equal to a lateral profile of the conductive canister; and at least one insulative structure disposed over a region of said conductive body;

a low-resistance, insulated conductor electrically coupled to said conductive body; and a connector electrically coupled to said conductor and configured to receive a proximal end of the subcutaneous lead assembly, said connector, said current collector, and said conductor configured to provide a low-resistance path from the defibrillation coil to the conductive canister to decrease the defibrillation threshold of the ICD.

14. A floating adapter configured to electrically couple a subcutaneous lead assembly to an implantable cardioverter defibrillation (ICD) including a conductive canister and a defibrillation coil, the ICD configured to be implanted proximate a patient's heart, the floating adapter comprising:

a current collector configured to be implanted adjacent the canister, comprising:

a conductive body comprising first and second opposing faces each having dimensions substantially equal to a lateral profile of the conductive canister; and at least one insulative structure disposed over a region of said conductive body;

a low-resistance, insulated conductor electrically coupled to said conductive body; and a connector electrically coupled to said conductor and configured to receive a proximal end of the subcutaneous lead assembly, said connector, said current collector, and said conductor configured to provide a low-resistance path from the defibrillation coil to the conductive canister to decrease the defibrillation threshold of the ICD; and wherein said conductive body comprises a substantially rectangular member having rounded edges and an outer edge, and wherein said insulative structure further comprises a peripheral frame extending around at least a portion of said outer edge.

15. A floating adapter according to claim 14 wherein said insulative structure further comprises a lattice of raised ribs coupled between an inner portion of said peripheral frame to form a plurality of windows to said conductive body.

* * * * *